(12) United States Patent
Akimoto (10) Patent No.: US 11,432,950 B2
(45) Date of Patent: Sep. 6, 2022

(54) STENT (71) Applicant: NIPRO CORPORATION, Osaka (JP)

(72) Inventor: Koji Akimoto, Osaka (JP)

(73) Assignee: NIPRO CORPORATION, Osaka (JP)

( * ) Notice: Subject to any disclaimer, the term of this patent is extended or adjusted under 35 U.S.C. 154(b) by 0 days.

(21) Appl. No.: 16/495,021

(22) PCT Filed: Mar. 22, 2018

(86) PCT No.: PCT/JP2018/011289
§ 371 (c)(1),
(2) Date: Sep. 17, 2019

(87) PCT Pub. No.: WO2018/174127
PCT Pub. Date: Sep. 27, 2018

(65) Prior Publication Data
US 2020/0375767 A1    Dec. 3, 2020

(30) Foreign Application Priority Data
Mar. 23, 2017 (JP) .............................. JP2017-058032

(51) Int. Cl.
*A61F 2/88* (2006.01)
*A61F 2/915* (2013.01)
(52) U.S. Cl.
CPC ............... *A61F 2/88* (2013.01); *A61F 2/915* (2013.01); *A61F 2002/9155* (2013.01); *A61F 2002/91575* (2013.01); *A61F 2250/0036* (2013.01); *A61F 2250/0037* (2013.01)

(58) Field of Classification Search
CPC ........................................................ A61F 2/88
See application file for complete search history.

(56) References Cited

U.S. PATENT DOCUMENTS

| 2004/0034402 | A1* | 2/2004 | Bales | ........................ A61F 2/91 |
| | | | | 623/1.2 |
| 2008/0097579 | A1 | 4/2008 | Shanley et al. | |
| 2010/0179643 | A1 | 7/2010 | Shalev | |
| 2011/0093059 | A1* | 4/2011 | Fischell | .................... A61F 2/91 |
| | | | | 623/1.15 |

(Continued)

FOREIGN PATENT DOCUMENTS

| CN | 102293694 A | 12/2011 |
| JP | 2011-502636 A | 1/2011 |

(Continued)

OTHER PUBLICATIONS

May 22, 2018 Search Report issued in International Patent Application No. PCT/JP2018/011289.

(Continued)

*Primary Examiner* — Leslie Lopez
(74) *Attorney, Agent, or Firm* — Oliff PLC (57) ABSTRACT

A stent having a line-shaped body that extends helically in a circumferential direction while reciprocating in an axial direction by continuously alternating straight parts and curved parts, wherein the plurality of straight parts in the line-shaped body have a substantially constant thickness throughout the entire stent, and a certain number of the plurality of curved parts in the line-shaped body have different thicknesses.

14 Claims, 7 Drawing Sheets

(56) References Cited

U.S. PATENT DOCUMENTS

2014/0358218 A1* 12/2014 Mitsudo .................. A61F 2/915
                                                    623/1.22
2015/0039078 A1   2/2015 Bales, Jr. et al.

FOREIGN PATENT DOCUMENTS

WO    2007/005800 A1    1/2007
WO    2012/096716 A2    7/2012

OTHER PUBLICATIONS

Sep. 24, 2019 International Preliminary Report on Patentability issued in International Patent Application No. PCT/JP2018/011289.
Dec. 2, 2020 Extended Search Report issued in European Patent Application No. 18770981.1.
Apr. 27, 2021 Office Action issued in Chinese Patent Application No. 201880019296.8.
Jun. 30, 2021 Office Action issued in Indonesian Patent Application No. P00201909037.
Aug. 4, 2021 Office Action issued in Japanese Patent Application No. 2019-506953.
Jan. 19, 2022 Office Action issued in Indian Patent Application No. 201917036921.

* cited by examiner

STENT

TECHNICAL FIELD

The present invention relates to a medical stent to be used, for example, to keep the inside diameter of the somatic lumen in an expanded state by being expanded and indwelled within the somatic lumen such as blood vessels.

BACKGROUND ART

Conventionally, a stent has been used in the percutaneous transluminal coronary angioplasty (PTCA), for example, to prevent a stenosis portion of the coronary artery from becoming restenosis due to recoil or the like after dilation with a balloon. The stent is constituted by, for example, a line-shaped body extending in a helical form in the circumferential direction while reciprocating in the axial direction. Specifically, as described in, for example, Japanese Domestic Publication of International Patent Application No. JP-A-2011-502636 (Patent Document 1), such a line-shaped body constitutes a wave-shaped skeleton structure reciprocating in the axial direction by straight parts and curved parts being provided alternately in a continuous manner.

Then, the stent inserted into the somatic lumen such as the coronary artery in the radially contracted state is pushed to radially expand with a balloon or undergoes self-expansion using the shape-memory effect of the stent itself so as to be indwelled in close contact with the inner wall surface of the somatic lumen. This will prevent restenosis caused by recoil or the like, thereby maintaining the inside diameter of the somatic lumen in the expanded state.

Meanwhile, regarding the stent described in Patent Document 1, in order to eliminate the inclination of the opposite end edges of the stent, the amplitude of the wave-shaped line-shaped body constituting the opposite end portions of the stent gradually changes, and the length of the straight part in the wave-shaped line-shaped body gradually decreases toward the distal end. When the amplitude of the wave-shaped line-shaped body is partially reduced, the deformation rigidity in the direction of expansion of the stent increases, so that there is a risk that the expanded shape of the stent may be distorted. Therefore, the stent described in Patent Document 1, discloses a mode in which the cross-sectional area of the line-shaped body gradually decreases toward the distal end of the line-shaped body where the amplitude of the wave-shaped line-shaped body is reduced.

However, examination by the present inventor has revealed that, when the cross-sectional area of the line-shaped body decreases, the basic strength in the skeleton structure of the stent is likely to be significantly reduced. Thus, the stent may be crushed due to, for example, bending deformation, external force in the axial direction exerted after being indwelled in the blood vessel.

Background Art Document

Patent Document

Patent Document 1: JP-A-2011-502636

SUMMARY OF THE INVENTION

Problem the Invention Attempts to Solve

The present invention has been developed in view of the above-described matters as the background, and it is an object of the present invention to provide a stent with a novel structure which is able to suppress distorted deformation during expansion while obtaining sufficient strength in the skeleton structure.

Means for Solving the Problem

A first preferred embodiment of the present invention provides a stent comprising a line-shaped body including a plurality of straight parts and a plurality of curved parts, the line-shaped body extending in a helical form in a circumferential direction while reciprocating in an axial direction by the straight parts and the curved parts alternately continuing, the stent being characterized in that: the straight parts of the line-shaped body have a substantially constant thickness throughout the stent; and a certain number of the curved parts of the line-shaped body has a different thickness from others.

According to the stent structured following the present preferred embodiment, it is possible to partially adjust the deformation rigidity of the stent in the direction of diameter enlargement at an appropriate location in the circumferential direction by varying the thicknesses of the curved parts of the line-shaped body constituting the stent. Therefore, it is also possible to enlarge the diameter more uniformly by, for example, suppressing distorted deformation during expansion of the stent.

In particular, among the plurality of curved parts provided to the line-shaped body, by making the thickness of the appropriate curved part different from that of the others, it is also possible to finely adjust the amount of deformation during expansion of the stent. On the other hand, the thickness of the plurality of straight parts provided to the line-shaped body is roughly constant throughout the stent. Thus, the basic strength of the skeleton structure exhibited by the straight parts can be sufficiently obtained, and concentration of stress or strain due to, for example, the straight part made thinner than the other straight parts or the like can also be avoided.

A second preferred embodiment of the present invention provides the stent according to the first preferred embodiment, wherein the curved parts include at least one of a thickened curved part and a thinned curved part relative to a largest number of basic-thick curved parts.

According to the stent structured following the present preferred embodiment, the basic embodiment of expanding deformation of the skeleton structure realized by the basic-thick curved parts is regarded as a reference, and it is possible to suppress a locally large amount of expanding deformation by the thickened curved part, to increase a locally small amount of expanding deformation by the thinned curved part, and the like so as to make an adjustment. Whereas the basic-thick curved part may have the roughly same thickness as the straight part, by setting the basic-thick curved part thicker than the straight part, it is possible to reduce deterioration in durability or strength due to strain or stress concentrating on approximately one point in the curved part during expanding deformation.

A third preferred embodiment of the present invention provides the stent according to the first or second preferred embodiment, wherein height dimensions of the straight parts and the curved parts of the line-shaped body are roughly constant, while width dimensions of the curved parts are made different so that the certain number of the curved parts has the different thickness.

According to the stent structured following the present preferred embodiment, the height dimension of the line-shaped body is roughly constant, thereby facilitating manufacture.

A fourth preferred embodiment of the present invention provides the stent according to any of the first through third preferred embodiments, wherein in a central portion of the stent, the straight parts have a roughly constant length dimension, while in opposite side portions of the stent, there is provided a long part where the straight part is elongated, and the curved part connected to the long part is thickened.

According to the stent structured following the present preferred embodiment, the thickened curved part suppresses the amount of deformation in the vicinity of the long part where the deformation during expansion is likely to be large, thereby avoiding excessive amount of deformation in the vicinity of the long part of the stent.

A fifth preferred embodiment of the present invention provides the stent according to the fourth preferred embodiment, wherein the long part is provided at a position approximately one round from a distal end of the line-shaped body in the circumferential direction of the stent, and the curved part connected to the long part is thickened.

For example, when the inclination direction of the end face of the stent is brought close to the vertical plane with respect to the central axis, by providing the long part in the portion approximately one round from the distal end of the line-shaped body in the circumferential direction of the stent, it is possible to reduce the situation in which the straight part in the portion close to the distal end of the line-shaped body is extremely short, or the like. Here, according the stent structured following the present preferred embodiment, by thickening the curved part connected to the long part, it is possible to suppress the amount of deformation of the long part during the expansion of stent.

A sixth preferred embodiment of the present invention provides the stent according to any of the first through fifth preferred embodiments, wherein in a central portion of the stent, the straight parts have a roughly constant length dimension, while in opposite side portions of the stent, there is provided a short part where the straight part is shortened, and the curved part connected to the short part is thinned.

According to the stent structured following the present preferred embodiment, the amount of deformation in the vicinity of the short part, in which the deformation during expansion is likely to be small, can be adjusted to increase by the thinned curved part.

A seventh preferred embodiment of the present invention provides the stent according to any of the first through sixth preferred embodiments, wherein the curved part, which is convex outward in a lengthwise direction of the stent at a position closest to a lengthwise distal end of the line-shaped body, is thinned.

For example, when the inclination direction of the end face of the stent is brought close to the vertical plane with respect to the central axis, in the portion which is close to the distal end of the line-shaped body, the straight part is likely to be short and finds it difficult to deform. Here, according to the stent structured following the present preferred embodiment, the curved part having an outwardly convex shape which is closest to the distal end in the lengthwise direction of the line-shaped body is thinned. By so doing, for the portion closest to the distal end of the line-shaped body where the straight part is likely to be short, it is possible to readily deform during expansion.

An eighth preferred embodiment of the present invention provides the stent according to any of the first through seventh preferred embodiments, wherein an inclination angle of a helix of the line-shaped body with respect to a central axis of the stent gradually increases toward an end thereof such that the inclination angle approaches a right angle with respect to the central axis of the stent.

According to the stent structured following the present preferred embodiment, even when passing through a bent part of a blood vessel or being indwelled in the bent part, for example, it is possible to minimize the phenomenon in which the axial end of the stent greatly deforms and floats radially outward or the like. The inclination angle of the helix can be changed in a continuous manner by the length of the straight part being gradually shorten in the opposite side portions of the stent, or alternatively can be changed in a stepwise manner by the straight part being lengthened partially in the circumferential direction.

A ninth preferred embodiment of the present invention provides the stent according to any of the first through eighth preferred embodiments, wherein the line-shaped body is provided with a linking part that links winding portions thereof to each other that are adjacent in a lengthwise direction of the stent.

According to the stent structured following the present preferred embodiment, the line-shaped body is provided with the linking part that links the winding portions thereof that are adjacent in the lengthwise direction of the stent. This may avoid the situation in which, during delivery or indwelling of the stent, the remote distance between the winding portions that are adjacent in the lengthwise direction in the line-shaped body becomes too large or too small. It would also be acceptable to set appropriate rupture strength to the linking part so that the linking part will be broken partially or entirely in an expanded state of the stent.

A tenth preferred embodiment of the present invention provides the stent according to any of the first through ninth preferred embodiments, wherein at each lengthwise end of the stent, when a lengthwise end of the line-shaped body is defined as a reference position of 0 degrees in the circumferential direction of the stent, with respect to a period of wave shape constituted by alternate continuation of the straight parts and the curved parts of the line-shaped body and reciprocating in the axial direction, the certain number of the curved parts having the different thickness are provided in plurality within a range of +1.5 periods to −3.5 periods in the circumferential direction of the stent.

According to the stent structured following the present preferred embodiment, it is possible to efficiently set the curved parts having different thicknesses in consideration of the position of the end of the line-shaped body so as to be able to avoid locally distorted deformation during expansion of the stent. In the present preferred embodiment, the direction in which the line-shaped body extends helically from the end toward the center of the stent is regarded as the positive side in the circumferential direction of the stent, while the direction in which the line-shaped body is hypothetically extended helically from the end is regarded as the negative side in the circumferential direction of the stent. Moreover, in the stent according to the present preferred embodiment, it is desirable that neither the thickened curved part nor the thinned curved part be provided in a region out of the range of +1.5 periods to −3.5 periods in the circumferential direction of the stent. This configuration may simplify the structure and the embodiment of deformation of the stent.

Effect of the Invention

According to the stent structured following the present invention, while ensuring the basic strength of the skeleton structure obtained by the straight parts of the line-shaped body, the amount of deformation during expansion of the stent can be partially adjusted by the curved parts having different thicknesses provided to the line-shaped body. It is also possible to improve the distorted deformation during expansion of the stent, for example.

BRIEF DESCRIPTION OF THE DRAWINGS

FIGS. 6A and 6B are views suitable for explaining the expanded state of the stent shown in FIG. 1, wherein FIG. 6A shows the stent having the structure of the present invention as Example, and FIG. 6B shows a stent as Comparative Example.

EMBODIMENTS FOR CARRYING OUT THE INVENTION

In order to clarify the present invention more specifically, practical embodiments of the present invention will be described in detail below in reference to the drawings.

Figure 1:
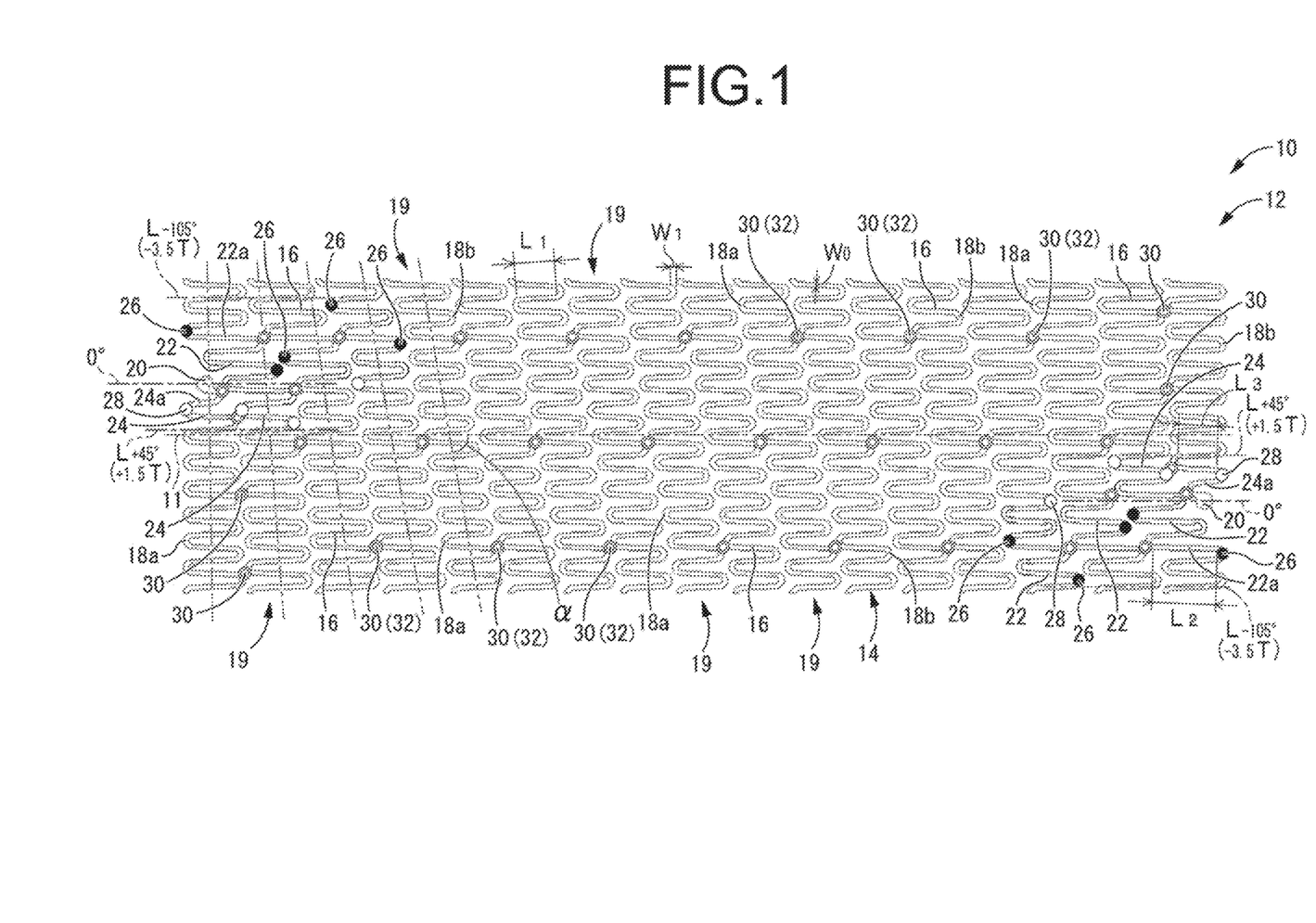
FIG. 1 is a developed view showing a stent as a first practical embodiment of the present invention by cutting to open the stent along one line on a circumference.

First, in FIG. 1, a stent 10 as a first practical embodiment of the present invention is shown as a developed view in which one circumferential part of the stent 10 is cut open along one cutting line extending in the direction of the central axis. The stent 10 includes a peripheral wall 12 having a generally round tubular shape overall. The stent 10 is configured to be delivered to a stenosis portion in a somatic lumen such as a blood vessel with its diameter constricted, and then to be indwelled with its diameter enlarged by being expanded in the radial direction, so that the stenosis portion is pushed open and maintained in an expanded state. In FIG. 1, the stent 10 is shown in an initial state in which the diameter is neither constricted nor enlarged. In the following description, the axial direction or the lengthwise direction of the stent 10 refers to the left-right direction in FIG. 1 in which a central axis 11 of the stent 10 extends.

Described more specifically, the peripheral wall 12 of the stent 10 has a basic skeleton comprising a single line-shaped body 14 extending in a helical form in the circumferential direction while reciprocating in the axial direction. The line-shaped body 14 includes straight parts 16 extending roughly straightly, and folded parts 18a, 18b serving as curved parts connecting the straight parts 16, 16 to each other that are adjacent in the circumferential direction. By the folded parts 18a, 18b being provided at the lengthwise opposite ends of the straight part 16, the straight parts 16 and the folded parts 18a, 18b alternately continue so as to constitute the basic skeleton of the stent 10 extending in a helical form in the circumferential direction while reciprocating in a wave form in the axial direction. For ease of explanation, the folded part that is convex toward one axial side (left side in FIG. 1) is identified as the folded part 18a, and the folded part that is convex toward the other axial side (right side in FIG. 1) is identified as the folded part 18b.

In the present practical embodiment, the folded parts 18a, 18b have a curved shape that is a roughly semicircular arc shape, and each of the folded parts 18a, 18b is a curved part of the line-shaped body 14. Besides, in the state shown in FIG. 1, the straight part 16 extends roughly parallel to the axial direction or slightly inclined with respect to the axial direction. In the present practical embodiment in particular, the reciprocation amplitude of the line-shaped body 14, namely, the length dimension $L_1$ (see FIG. 1) of the straight part 16 is roughly constant at least in the axially central portion of the stent 10, and the stent 10 have a roughly uniform wave shape at least in a region of the plurality of rounds positioned in the axially central portion of the stent 10. By the line-shaped body 14 extending in a helical form in the circumferential direction while reciprocating in the axial direction, there are formed band-shaped bodies 19 serving as winding portions that extend in a helical form in the circumferential direction with a width corresponding to the amplitude of the line-shaped body 14, namely, the length dimension of the straight part 16. The band-shaped bodies 19, 19 arranged adjacent to each other in the axial direction are remote by a predetermined distance (pitch) in the axial direction. In the present practical embodiment, the structure of reciprocation amplitude of the line-shaped body 14 is formed with a generally constant pitch throughout the stent 10.

In the present practical embodiment, the line-shaped body 14 is an elongated member extending with a generally rectangular, thin-plate cross sectional shape. Specifically, the height dimension of the line-shaped body 14 (the straight parts 16 and the folded parts 18a, 18b) is roughly constant across the entire length of the stent 10. Also, the width dimensions $W_0$ (see FIG. 1) of the straight parts 16 in the line-shaped body 14 are made substantially equal across the entire length of the stent 10. Therefore, in the line-shaped body 14, the thicknesses (cross-sectional areas) of the straight parts 16 are substantially equal across roughly the entire length of the stent 10. The stent 10 is appropriately provided with a linking part 30, a friable part 32, etc., which will be described later, and at opposite ends of the line-shaped body 14, a disc part 20 having a diameter larger than the width dimension $W_0$ is provided as necessary. While permitting variations in width dimension and the like due to provision of such components, the width dimensions $W_0$ of all the straight parts 16 are substantially constant.

Besides, for a largest number of basic-thick folded parts 18a, 18b, which are positioned at least in the axially central portion of the stent 10, the width dimension of the folded parts 18a, 18b is set to a width dimension $W_1$ that is slightly larger than the width dimension of the straight part 16. In the present practical embodiment, at the circumferentially opposite ends of the folded part 18a/18b, the part bounded by the straight part 16 has roughly the same width dimension as that of the straight part 16, while in a predetermined length region at the lengthwise center of the folded part 18a/18b, the width dimension is set to the width dimension $W_1$, which is the largest. The width dimension $W_1$ of the basic-thick folded part 18a/18b is preferably set within the range such that $1.0\,W_0 < W_1 \leq 1.5\,W_0$ (more than 100% and not more than 150%) with respect to the width dimension $W_0$ of the straight part 16, and more preferably set 110% to 140% with respect to the width dimension $W_0$ ($1.0\,W_0 < W_1 \leq 1.4\,W_0$). Incidentally, in the present practical embodiment, $W_1/W_0=1.25$.

By making the basic thickness $W_1$ of the folded part 18a/18b larger than the thickness $W_0$ of the straight part 16 in this way, bending stress and strain during expansion of the stent are inhibited from concentrating on one point roughly in the center of the folded part 18a/18b. Accordingly, by dispersing the stress and strain in the lengthwise direction of the folded part 18a/18b, the strength and durability of the stent may be improved, or the like. Further, in the present practical embodiment, the thickness smoothly changes between the straight part 16 and the folded part 18a/18b, thereby also avoiding stress concentration due to sudden change in cross-sectional area in the lengthwise direction of the line-shaped body 14.

Furthermore, the number of waves (number of turns) in the circumferential direction in one round, that is, the number of repeating units of the periodic structure in one round of the line-shaped body 14 is not limited at all, but in the stent 10 of the present practical embodiment, the number of waves is twelve, which is approximately constant across the entire length.

Moreover, the lengthwise opposite ends of the line-shaped body 14 are each provided with the disc part 20 which is expanded in comparison with its middle portion and has a generally circular disk shape. The disc part 20 may reduce the pressure due to the distal end of the line-shaped body 14, which is exerted on the living tissues with the stent indwelled, and facilitate the handling of the line-shaped body 14, and the like.

The line-shaped body 14 can be formed of a biodegradable resin, a synthetic resin or the like, but is preferably formed of a metal with superior biocompatibility such as stainless steel, cobalt-chrome alloy, and Ni—Ti alloy (i.e. a bioinert metal with no toxicity to living tissues).

In this way, the line-shaped body 14 extends in a helical form in the circumferential direction while reciprocating in the axial direction, so as to form the peripheral wall 12 extending in the axial direction and having a generally round tubular shape overall. Whereas the axial dimension of the stent 10 (peripheral wall 12) is not limited at all, it is approximately 18 mm in the present practical embodiment.

The peripheral wall 12 can be obtained by, for example, using a sleeve-shaped raw tube made of generally round tubular metal member or the like, and cutting out the peripheral wall of the raw tube with a laser or the like so as to form the line-shaped body 14 having a predetermined shape. However, the manufacturing method of the stent 10 is not limited to the above-described laser cutting, but conventionally known manufacturing methods of a stent such as electroforming and etching may be adopted.

Furthermore, in the stent 10 of the present practical embodiment, the inclination angle $\alpha$ (see FIG. 1) of the helix of the line-shaped body 14 is made to change in the axial direction. That is, in the axially central portion of the stent 10, the helix of the line-shaped body 14 extends with a roughly constant inclination angle, while in the axially opposite side portions, the inclination angle gradually increases toward the axial end and approaches a right angle. Then, at the axially opposite ends of the stent 10, the inclination angle $\alpha$ of the helix of the line-shaped body 14 is configured to be an approximately right angle ($\alpha \approx 90$ degrees) with respect to the central axis 11.

With this configuration, the axially opposite end faces of the peripheral wall 12 of the stent 10 spread in the roughly axis-perpendicular direction. In other words, in the line-shaped body 14, the apexes of the folded parts 18a, 18b, which are positioned at the axially opposite ends of the stent in a row in the circumferential direction in an outwardly convex mode, are all roughly positioned on the same plane spreading in the axis-perpendicular direction.

The inclination angle $\alpha$ of the helix refers to, for example, the angle of the helix shown by the chain double-dashed lines in FIG. 1 that connect the axial center of each straight part 16 of the line-shaped body 14 adjacent to each other in the central portion in the axis-perpendicular direction (vertical direction) in FIG. 1, and is represented by the value of "90 degrees minus lead angle of helix". In FIG. 1, the inclination angle $\alpha$ of the helix is indicated as an angle relative to the direction line of the central axis 11 shown by the dot-and-dash line.

Here, in order to make the inclination angle $\alpha$ of the helix different in the axial direction as described above, in the stent 10, the length dimension of the straight part 16 is made different in the axial direction. That is, in the present practical embodiment, in the axially central portion of the stent 10, the length dimension of the straight part 16 is roughly constant ($L_1$), and the inclination angle $\alpha$ of the helix is also roughly constant. Meanwhile, in the axially opposite side portions of the stent 10, the length dimension of the straight part 16 is made different from the length dimension ($L_1$) of the straight part 16 in the axially central portion, so that the inclination angle $\alpha$ of the helix gradually approaches a right angle toward the axially opposite ends.

Specifically, on the axially opposite side portions of the stent 10, the line-shaped body 14 is provided with a long part 22 whose length dimension $L_2$ is made larger than that of the straight part 16 in the axially central portion ($L_1 < L_2$) and extends in a straight line, and a short part 24 whose length dimension $L_3$ is made shorter than that of the straight part 16 in the axially central portion ($L_1 > L_3$) and extends in a straight line.

Specifically, the straight part 16 of the line-shaped body 14 comprises [1] a portion in the axially central portion having a roughly constant, basic length dimension ($L_1$), [2] a portion in the axially opposite side portions having a length dimension ($L_2$) larger than the basic length dimension (long part 22), and [3] a portion in the axially opposite side portions having a length dimension ($L_3$) smaller than the basic length dimension (short part 24).

Figure 2:
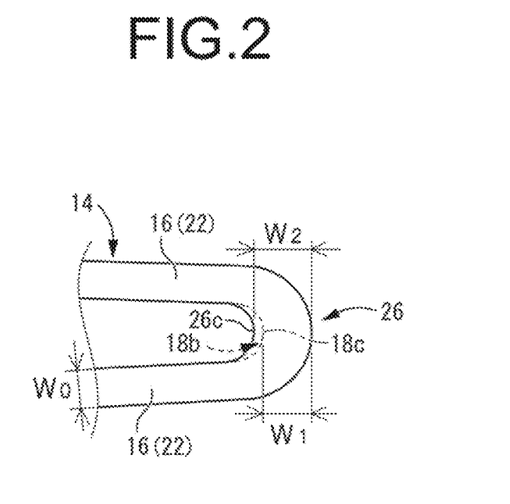
FIG. 2 is a view suitable for explaining a specific example of a wide part (thickened curved part) of the stent shown in FIG. 1.

As shown in FIG. 2, at least one of the folded parts 18a, 18b provided to the lengthwise opposite ends of the long part 22 constitutes a wide part 26 whose width dimension $W_2$ is made larger than that of the basic-thick folded parts 18a, 18b (shown by the chain double-dashed line in FIG. 2) provided to the axially central portion of the stent 10 ($W_1 < W_2$). In the present practical embodiment, a plurality of the long parts 22 are provided in the stent 10, and among the plurality of folded parts 18a, 18b provided to the lengthwise opposite ends of the plurality of long parts 22, a suitable number thereof constitute the wide parts 26.

In the present practical embodiment, in the line-shaped body 14, the width dimension of the straight part 16 (long part 22) is roughly equally set to $W_0$ across the entire length of the stent 10, and the basic thickness of the folded parts 18a, 18b (basic width dimension) $W_1$ is made larger than $W_0$. Moreover, the width dimension $W_2$ of the wide part 26 is made larger than the basic thickness $W_1$. Therefore, their relationship is expressed by "$W_0<W_1<W_2$".

Besides, in the present practical embodiment, the width dimension $W_2$ of the wide part 26 (folded parts 18a, 18b) is made larger than the basic thickness $W_1$ across roughly the entire length in the lengthwise direction. In the practical embodiment in particular, the wide part 26 is formed with the thickness dimension $W_2$ by thickening the radially inner side of a curved shape of the folded parts 18a, 18b having the basic thickness dimension $W_1$. That is, the radius of curvature of the radially inner surface 26c in the curved shape of the wide part 26 having the increased width dimension is made larger than the radius of curvature of the radially inner surface 18c in the curved shape of the folded parts 18a, 18b having the basic thickness. Note that the radius of curvature of the radially outer surface in the curved shape of the folded parts 18a, 18b having the basic thickness and the radius of curvature of the radially outer surface in the curved shape of the wide part 26 having the increased width dimension are roughly equal. The width dimension $W_2$ of the wide part 26 in the present practical embodiment is made larger than the basic thickness $W_1$ across substantially the entire length of the wide part 26. In particular, in the present practical embodiment, the lengthwise center of the wide part 26 has the maximum width dimension $W_2$.

In particular, in the present practical embodiment, the height dimension of the line-shaped body 14 is made equal across the entire length of the stent 10. Thus, by the width dimension being made different as described above, the formation zone of the wide part 26 is made widest and thickest (the cross-sectional area is made largest) in the lengthwise direction of the line-shaped body 14. Also, in the present practical embodiment, the wide part 26 constitutes a thick line part (thickened curved part) in which the thickness of the line-shaped body 14 is made larger than that of the basic-thick folded parts 18a, 18b provided in the axially central portion.

Further, the width dimension $W_2$ of the wide part 26 is preferably set within the range such that $1.0\,W_1<W_2\leq1.5\,W_1$ (more than 100% and not more than 150%) with respect to the basic width dimension $W_1$ of the folded parts 18a, 18b in the axially central portion of the stent 10, and more preferably set within the range of 110% to 130% ($1.1\,W_1<W_2\leq1.3\,W_1$). In the present practical embodiment, the width dimension $W_2$ of the wide part 26 is set to 120% of the basic width dimension $W_1$ of the folded parts 18a, 18b in the axially central portion of the stent 10 ($W_2=1.2\,W_1$). By setting the width dimension $W_2$ of the wide part 26 within the aforementioned range, localized large deformation during expansion of the stent 10 is suppressed as will be described later.

Figure 3:
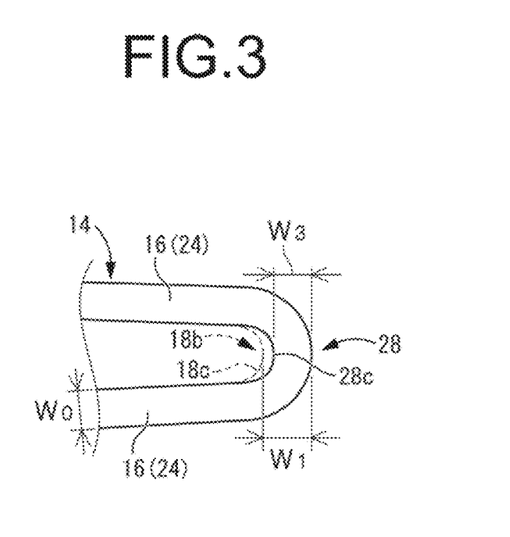
FIG. 3 is a view suitable for explaining a specific example of a narrow part (thinned curved part) of the stent shown in FIG. 1.

On the other hand, as shown in FIG. 3, at least one of the folded parts 18a, 18b provided to the lengthwise opposite ends of the short part 24 constitutes a narrow part 28 whose width dimension $W_3$ is made smaller than that of the basic-thick folded parts 18a, 18b (shown by the chain double-dashed line in FIG. 3) provided to the axially central portion of the stent 10 ($W_3<W_1$). In the present practical embodiment, a plurality of the short parts 24 are provided in the stent 10, and among the plurality of folded parts 18a, 18b provided to the lengthwise opposite ends of the plurality of short parts 24, a suitable number thereof constitute the narrow parts 28.

In the present practical embodiment, since the basic thickness (basic width dimension) $W_1$ of the folded parts 18a, 18b is made larger than the width dimension $W_0$ of the straight part 16 (long part 22) in the line-shaped body 14, it would be acceptable as long as the width dimension $W_3$ of the narrow part 28 is smaller than the basic width dimension $W_1$ of the folded part. However, in preferred practice, it is desirable that the width dimension $W_3$ of the narrow part 28 be set equal to or larger than the width dimension $W_0$ of the straight part 16 ($W_0\leq W_3\leq W_1$). By making the width dimension $W_3$ of the narrow part 28 equal to or larger than the width dimension $W_0$ of the straight part 16, it would be possible to reduce or avoid locally excessive deformation due to concentration of stress or strain on the narrow part 28 during expansion of the stent.

That is, in the present practical embodiment, the narrow part 28 is formed with the thickness dimension $W_3$ by thinning the radially inner side of the curved shape of the folded parts 18a, 18b having the basic thickness dimension $W_1$. In the present practical embodiment in particular, the width dimension $W_3$ of the narrow part 28 is made equal to or larger than the width dimension $W_0$ of the straight part 16. That is, the radius of curvature of the radially inner surface 28c in the curved shape of the narrow part 28 having the decreased width dimension is made smaller than the radius of curvature of the radially inner surface 18c in the curved shape of the folded parts 18a, 18b having the basic thickness. Note that the radius of curvature of the radially outer surface in the curved shape of the folded parts 18a, 18b having the basic thickness and the radius of curvature of the radially outer surface in the curved shape of the narrow part 28 having the decreased width dimension are roughly equal.

In particular, in the present practical embodiment, the height dimension of the line-shaped body 14 is made equal across roughly the entire length of the stent 10. Thus, by the width dimension being made different as described above, the formation zone of the narrow part 28 is made narrowest and thinnest (the cross-sectional area is made smallest) among the plurality of folded parts 18a, 18b. Also, in the present practical embodiment, the narrow part 28 constitutes a thin line part (thinned curved part) in which the thickness is made smaller than that of the basic-thick folded parts 18a, 18b provided in the axially central portion.

The width dimension $W_3$ of the narrow part 28 in the present practical embodiment is made smaller than the basic thickness $W_1$ across substantially the entire length of the narrow part 28. In particular, in the present practical embodiment, the lengthwise center of the narrow part 28 has the minimum width dimension $W_3$.

Further, the width dimension $W_3$ of the narrow part 28 is preferably set within the range such that $0.5\,W_1\leq W_3<1.0\,W_1$ (50% or more and less than 100%) with respect to the width dimension $W_1$ of the basic-thick folded parts 18a, 18b in the axially central portion of the stent 10, and more preferably set within the range of 70% to 90% ($0.7\,W_1\leq W_3\leq0.9\,W_1$). In the present practical embodiment, the width dimension $W_3$ of the narrow part 28 is set to 80% of the width dimension $W_1$ of the basic-thick folded parts 18a, 18b ($W_3=0.8\,W_1$). By setting the width dimension $W_3$ of the narrow part 28 within the aforementioned range, localized lack of deformation during expansion of the stent 10 is reduced as will be described later.

The positions of the wide part 26 and the narrow part 28 may be appropriately set such that local distortion of deformation is moderated in consideration of mode of deformation, the width dimension to be set, and the like during expansion of the stent 10. Thus, the positions are not limited in any way, and the wide parts 26 and the narrow parts 28 are respectively formed at the positions indicated by black circles and white circles in FIG. 1.

That is, the wide part 26 and the narrow part 28 in the present practical embodiment are provided in the region where the length dimensions of the straight parts 16 are made different (namely, the long part 22 and the short part 24 are provided), and the inclination angle α of the helix of the line-shaped body 14 gradually changes. The size of such a region is not limited at all, but it is sufficient to be at least one round in the circumferential direction at the lengthwise opposite side portions of the stent 10, preferably at least two rounds in the circumferential direction, and more preferably at least three rounds. In the present practical embodiment, the long part 22 and the short part 24 as well as the wide part 26 and the narrow part 28 are provided over the region of approximately three rounds in the circumferential direction of the stent 10 from the axially opposite ends thereof. With this configuration, it is possible to avoid sudden change in the inclination angle α of the helix of the line-shaped body 14, and to set the amount of change in the inclination angle per round to 5 degrees or less, for example, thereby more smoothly producing deformation or expansion of the stent 10 throughout its entirety.

Besides, as described above, the present practical embodiment adopts a structure in which the inclination angle α of the helix of the line-shaped body 14 increases toward the axial end at the axially opposite side portions. By so doing, in the region of approximately two waves (number of turns) from the lengthwise end of the line-shaped body 14 in the direction of extension of the helix (on the left side in FIG. 1, which is one axial side, the direction going downward from the disc part 20, while on the right side in FIG. 1, which is the other axial side, the direction going upward from the disc part 20), the straight part 16 constitutes the short part 24 whose length dimension is shortened. Specifically, it is preferable that two or three straight parts 16 positioned in the direction of extension of the helix with respect to the disc part 20 constitute the short parts 24, and at least one straight part 16 adjacent to the disc part 20 in the direction of extension of the helix constitutes a short part 24a. Then, in the short part 24a adjacent to the disc part 20 in the direction of extension of the helix, regarding the folded parts (curved parts) 18a, 18b connected to the short part 24a, the curved part which is convex outward in the axial direction (the folded part 18a in the short part 24a on the left side in FIG. 1, and the folded part 18b in the short part 24a on the right side in FIG. 1) constitutes the narrow part 28. That is, the curved parts (folded parts) 18a, 18b, which are convex outward in the lengthwise direction of the stent 10 at the position closest to the distal end (the lengthwise end) of the line-shaped body 14, constitute the narrow part 28.

On the other hand, in the present practical embodiment, in the portion approximately one round in the circumferential direction from the lengthwise end of the line-shaped body 14, over the region of approximately two waves (number of turns), the straight part 16 constitutes the long part 22 whose length dimension is increased. Specifically, it is preferable that two or three straight parts 16 positioned on the opposite side to the direction of extension of the helix with respect to the disc part 20 constitute the long parts 22, and at least one straight part 16 adjacent to the disc part 20 on the opposite side to the direction of extension of the helix constitutes a long part 22a. Then, in the long part 22a adjacent to the disc part 20 on the opposite side to the direction of extension of the helix, regarding the folded parts (curved parts) 18a, 18b connected to the long part 22a, the curved part which is convex outward in the axial direction (the folded part 18a in the long part 22a on the left side in FIG. 1, and the folded part 18b in the long part 22a on the right side in FIG. 1) constitutes the wide part 26. That is, the long part 22a is provided at the position approximately one round from the distal end (the lengthwise end) of the line-shaped body 14 in the circumferential direction of the stent 10, and the curved parts (folded parts) 18a, 18b connected to the long part 22a constitute the wide parts 26. In particular, in the present practical embodiment, the portion approximately one round in the circumferential direction from the lengthwise end (disc part 20) of the line-shaped body 14 constitutes the long part 22a adjacent to the disc part 20 on the opposite side to the direction of extension of the helix, and the wide part 26 is connected to the long part 22a. However, for example, the portion approximately one round in the circumferential direction from the lengthwise end of the line-shaped body 14 may be remote from the disc part 20 in the circumferential direction by, for example, two or three waves (number of turns).

Figure 4A:
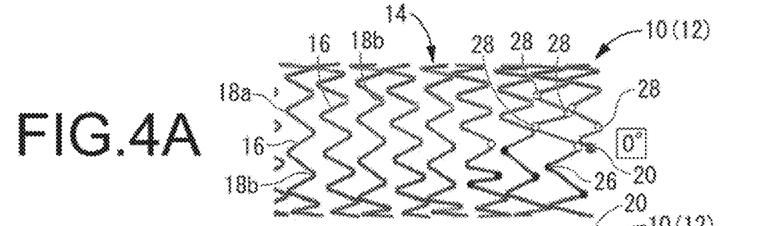
FIGS. 4A-4D are views suitable for explaining an expanded state of the stent shown in FIG. 1.

Moreover, FIGS. 4A-4D show the simulation results which simulated the expanded state of the stent 10 according to the present practical embodiment on the computer. Here, FIG. 4A shows a state in which the disc part 20 on the other axial side of the stent 10 is positioned at the front in the drawing, and FIGS. 4B-4D respectively show states in which the stent 10 is rotated in the circumferential direction by the angle noted on the right side of FIGS. 4B-4D (90 degrees, 180 degrees, and 270 degrees, respectively) from the state shown in FIG. 4A. Although only the end on the other axial side of the stent 10 is shown in FIGS. 4A-4D, the end on one axial side is rotationally symmetrical with respect to FIGS. 4A-4D. In FIGS. 4A-4D as well, the wide part 26 and the narrow part 28 are indicated by black circles and white circles, respectively.

Figure 4B:
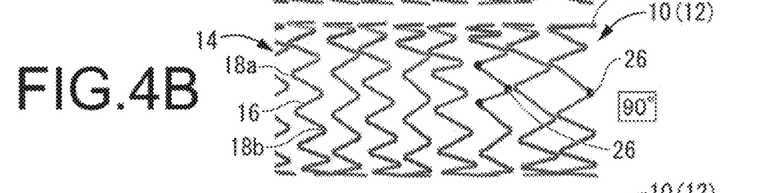
Figures 4C, 4D:
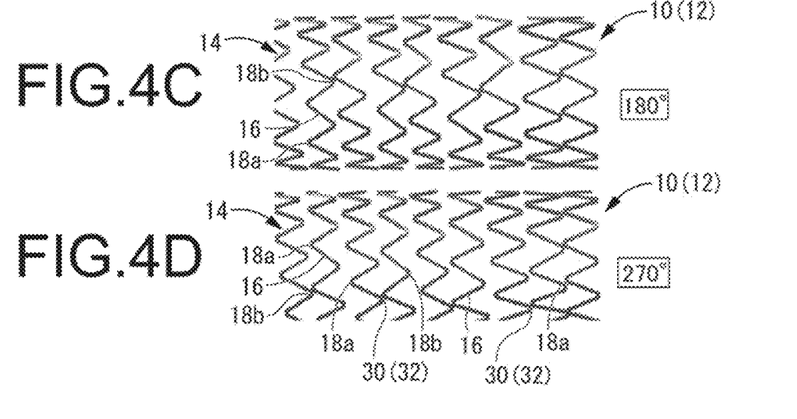

As apparent from FIGS. 4A-4D, the wide part 26 and the narrow part 28 (namely, the long part 22 and the short part 24) are shown only in FIGS. 4A and 4B. Specifically, in the present practical embodiment, as shown in FIG. 1, in the initial state of the stent 10, the end where the disc parts 20 is formed (the lengthwise distal end of the line-shaped body 14), which is provided at each axial end is regarded as ±0 degrees, which is a reference position in the circumferential direction. When the direction of extension of the helix of the line-shaped body 14 in the circumferential direction is regarded as a plus direction, while the hypothetically extended direction opposite to the direction of extension of the helix of the line-shaped body 14 in the circumferential direction is regarded as a minus direction, the wide part 26 and the narrow part 28 are provided within the range of +45 degrees to −105 degrees positioned on circumferentially opposite sides sandwiching ±0 degrees. Here, such a numerical range does not correspond to the numerical values noted on the right side of FIGS. 4A-4D.

This means that, when a period (T) of wave shape constituted by alternate continuation of the straight parts 16 and the curved parts 18a, 18b of the line-shaped body 14 and reciprocating in the axial direction is regarded as a unit, the substantially all the wide parts 26 and narrow parts 28 are provided within the range of +1.5 periods to −3.5 periods in the circumferential direction of the stent with respect to the position of ±0 degrees, which is the reference position. That is, the stent 10 of the present practical embodiment has a skeleton structure of 12 waves/round, and the period (T) of one wave is 30 degrees. For reference, in FIG. 1, in addition to a straight line of ±0 degrees indicating the reference position in the circumferential direction of the line-shaped body 14 in the helix direction, straight lines indicating +45 degrees and −105 degrees in the circumferential direction are shown as $L_{+45}$ and $L_{-105}$, respectively.

That is, in the stent 10 of the present practical embodiment, in order to set the inclination angle α of the helix of the line-shaped body 14 at the axially opposite ends to approximately a right angle with respect to the central axis 11, the length dimensions of the straight parts 16 of the line-shaped body 14 at the opposite ends of the stent 10 are made different. That is, with respect to the lengthwise distal end of the line-shaped body 14, the plurality of short parts 24 are provided within the range of ±0 degrees to +45 degrees in the helix direction of the line-shaped body 14, and at the same time in a region covering three rounds in the circumferential direction. Then, with regard to an appropriate number of the short parts 24, the folded part (curved part) 18a/18b connected to at least one of the lengthwise ends constitutes the narrow part 28. On the other hand, with respect to the lengthwise distal end of the line-shaped body 14, the plurality of long parts 22 are provided within the range of ±0 degrees to −105 degrees in the helix direction of the line-shaped body 14, and at the same time in a region covering three rounds in the circumferential direction. Then, with regard to an appropriate number of the long parts 22, the folded part (curved part) 18a/18b connected to at least one of the lengthwise ends constitutes the wide part 26.

Moreover, the line-shaped body 14 of the present practical embodiment is provided with a plurality of linking parts 30 in the lengthwise direction. The linking part 30 is provided so as to link the band-shaped bodies 19, 19 serving as the winding portions to each other that are adjacent in the axial direction, and in the present practical embodiment in particular, the linking part 30 is provided so as to link the folded part 18a and the folded part 18b to each other that are adjacent in the axial direction. The linking part 30 is formed at every predetermined number of folded parts 18a (18b), and in the present practical embodiment, as shown in FIG. 1, the linking part 30 is provided at every seven folded parts 18a (18b) in the axially central portion of the stent 10, and at every one or two folded parts 18a (18b), or continuously, in the axially opposite ends of the stent 10. In FIG. 1, the positions of the linking parts 30 are shown by double circles. With this arrangement, the plurality of linking parts 30 are evenly provided at generally constant intervals in the lengthwise direction of the line-shaped body 14.

Figure 5:
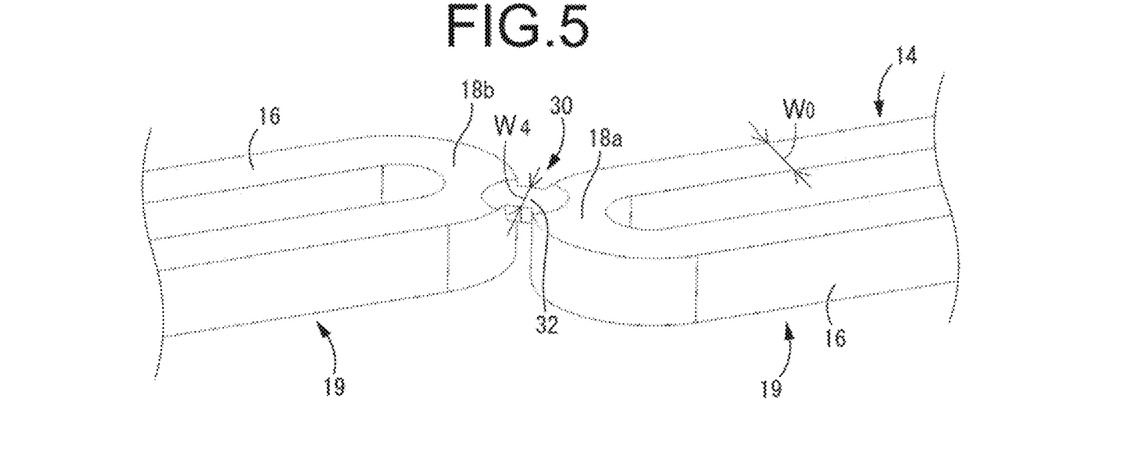
FIG. 5 is a view suitable for explaining a specific example of a linking part of the stent shown in FIG. 1.

While the structure of the linking part 30 is not limited in any way, in the present practical embodiment, as shown in FIG. 5, a friable part 32 is provided to the linking part 30 in the axially central portion of the stent 10. The friable part 32 is a portion having a lower mechanical strength than the line-shaped body 14, and in the present practical embodiment, the entire linking part 30 located in the axially central portion of the stent 10 is constituted by the friable part 32. With this configuration, when the stent 10 is indwelled at a bent part etc. in a somatic lumen and bent in the lengthwise direction or the like, the friable part 32 is arranged to be broken preferentially.

In the friable part 32 of the present practical embodiment, the width dimension $W_4$ (see FIG. 5) is made smaller than the width dimension $W_1$ of the folded part 18a/18b in the line-shaped body 14, and the height dimension is also made smaller than that of the line-shaped body 14. The width dimension $W_4$ and the height dimension of the friable part 32 are not limited at all, but for example, it is preferable that the width dimension $W_4$ of the friable part 32 be 0.2 to 0.9 times the width dimension $W_1$ of the folded part 18a/18b of the line-shaped body 14, and the height dimension of the friable part 32 be 0.2 to 0.7 times that of the folded part 18a/18b of the line-shaped body 14.

Thus, by making the friable part 32 narrower and thinner than the line-shaped body 14 in this way, the cross-sectional area of the friable part 32 is made smaller than that of the line-shaped body 14. With this configuration, the mechanical strength of the friable part 32 is lower than that of the line-shaped body 14. Preferably, the cross-sectional area of the friable part 32 is 0.01 to 0.7 times that of the basic-thick folded part 18a/18b in the line-shaped body 14.

The friable part 32 is formed by, for example, mutually welding the curved parts 18a, 18b that are adjacent in the axial direction in the line-shaped body 14 with a laser. By so doing, the friable part 32 can be easily formed by after-processing, and the friable part 32 can be formed in desirable shape and size by appropriately controlling the irradiation time, intensity and the like of the laser. Accordingly, the timing of breakage of the friable part 32 can be readily controlled.

On the other hand, it is preferable that the linking parts 30 positioned at the axially opposite ends of the stent 10 do not have the friable part 32. That is, for example, the width dimension and the height dimension of the linking part 30 may be made roughly equal to those of the folded part 18a/18b of the line-shaped body 14, and the linking part 30 may have mechanical strength similar to that of the line-shaped body 14. With this configuration, the strength at the axially opposite ends of the stent 10 is improved, thereby suppressing the distorted deformation at the axially opposite ends of the stent 10 when the stent 10 is bent in the lengthwise direction, or the like.

The stent 10 structured as described above is placed externally about a balloon of a balloon catheter for stent expansion (not shown) and inserted into a stenosis portion of a somatic lumen (for example, a blood vessel etc.). Then, by expanding the balloon of the balloon catheter for stent expansion, the stent 10 placed externally about the balloon undergoes diameter enlarging deformation, so as to come into close contact with the blood vessel wall. Subsequently, the balloon is deflated and withdrawn from the stent 10, whereby the stent 10 is indwelled at the stenosis portion of the blood vessel to maintain the somatic lumen in the expanded state, and to prevent occurrence of restenosis at the stenosis portion, and the like.

Figure 6A:
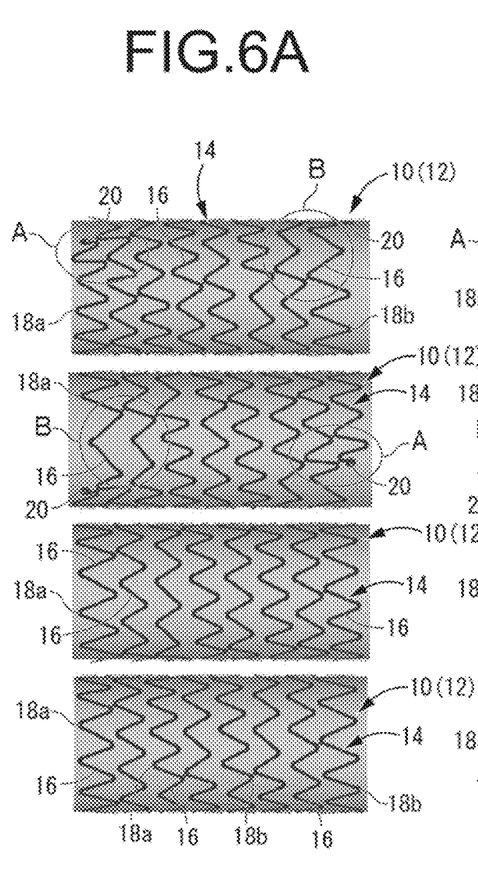
Figure 6B:
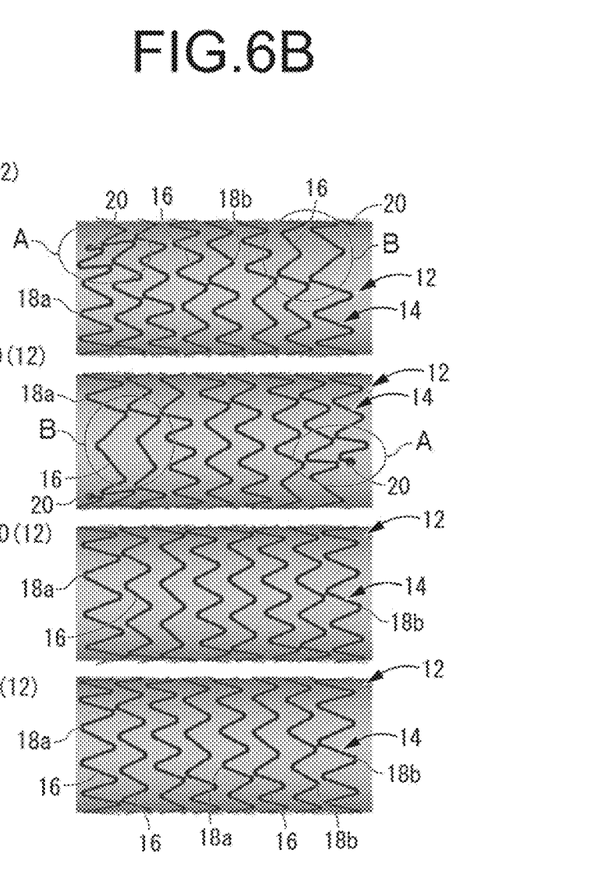

FIG. 6A shows simulation results of the expanded state of the stent 10 having such a structure, while FIG. 6B shows a stent having no thick line part or thin line part as a stent of Comparative Example. In the stents shown in FIGS. 6A and 6B, the structures other than the thick line part and the thin line part are identical. Besides, in FIGS. 6A and 6B, similar to FIGS. 4A-4D, the four drawings show the cases in which the top drawing is the front (0 degrees), and the others are the drawings rotated by every 90 degrees toward the bottom. However, the position of the front (0 degrees) is different from that in FIG. 4A.

Specifically, in FIGS. 6A and 6B, by comparing the regions encircled by the circle A with each other, it will be understood that the deformation of line-shaped body 14 is promoted more in FIG. 6A than in FIG. 6B. The region encircled by the circle A is the region where the short parts are provided in the line-shaped body. As shown in FIG. 6B, in the case in which the short parts are provided for the purpose of making the axially opposite ends of the stent nearly perpendicular to the axial direction, there is a risk that the line-shaped body may not sufficiently expand. On the other hand, in FIG. 6A, the narrow part 28 is provided to the short part 24, so as to facilitate expanding deformation, thereby making it possible to increase the amount of displacement of the straight part 16 (short part 24) connected to the narrow part 28. By so doing, regarding the region encircled by the circle A where the expanding deformation may be locally insufficient, the uniformity of the expanding deformation with respect to the other portions can be improved.

On the other hand, in FIGS. 6A and 6B, by comparing the regions encircled by the circle B with each other, it will be understood that the deformation of line-shaped body 14 is suppressed more in FIG. 6A than in FIG. 6B. The region encircled by the circle B is the region where the long parts are provided in the line-shaped body. As shown in FIG. 6B, if the long parts are only provided for the purpose of making the axially opposite ends of the stent nearly perpendicular to the axial direction, there is a risk that the line-shaped body may excessively expand. On the other hand, in FIG. 6A, the wide part 26 is provided to the long part 22, so as to suppress expanding deformation, thereby making it possible to decrease the amount of displacement of the straight part 16 (long part 22) connected to the wide part 26. By so doing, regarding the region encircled by the circle B where the expanding deformation may be excessive, the uniformity of the expanding deformation with respect to the other portions can be improved.

With the stent 10 of the present practical embodiment constructed as described above, by providing the wide part 26 and the narrow part 28 to the curved parts 18a, 18b of the line-shaped body 14, uniformity in diameter enlargement can be improved as described above. In particular, since the thickness or the like of the straight part 16 is not changed when the wide part 26 and the narrow part 28 are provided, shape retention, crushing strength or the like exhibited by the basic skeleton structure on the axially opposite side portions of the stent 10 can be stably obtained, as well as it becomes easy to adjust the design and expanding deformation.

Besides, the portion having different thickness such as the wide part 26 and the narrow part 28 is provided to the curved part (folded part) 18a/18b instead of the straight part 16. Thus, when the diameter of the stent 10 is enlarged, it is possible to effectively prevent the stent 10 from being bent at the straight part 16. In particular, since such a change in thickness is realized not by changing the height dimension but by changing the width dimension, the stent 10 can be easily manufactured by laser cutting or the like.

Moreover, in the present practical embodiment, since the inclination angle α of the helix of the line-shaped body 14 is approximately a right angle with respect to the central axis 11 at the axially opposite ends, the line-shaped body 14 can be effectively prevented from floating or the like during bending deformation of the stent 10. In particular, the inclination angle α of the helix of the line-shaped body 14 gradually increases toward the axially opposite ends. This may avoid a sudden change in length of the straight part 16, thereby further improving the uniformity in diameter enlargement.

Besides, as described above, by forming the axially opposite ends in a shape perpendicular to the central axis 11, at the lengthwise opposite ends of the line-shaped body 14, the length dimension of the straight part 16 in the portion adjacent thereto in the direction of extension of the helix is likely to be short, or the length dimension of the straight part 16 in the portion adjacent thereto on the opposite side to the direction of extension of the helix is likely to be long. However, by providing the narrow part 28 and the wide part 26 to the short part 24a and the long part 22a respectively, the stent 10 can be enlarged in diameter even more reliably and uniformly.

In particular, the wide part 26 and the narrow part 28 (the long part 22 and the short part 24) are provided within the range of a predetermined angle in the circumferential direction with respect to the lengthwise opposite ends of the line-shaped body 14. Accordingly, the wide part 26 and the narrow part 28 can be arranged efficiently, and change in length dimension of the straight part 16, change in width dimension of the folded part 18a/18b, and the like can also be kept to a minimum.

Furthermore, in the present practical embodiment, there is provided the linking part 30 linking the band-shaped bodies 19, 19 to each other that are adjacent in the axial direction, thereby improving the overall shape stability of the stent 10 as well.

Figure 7:
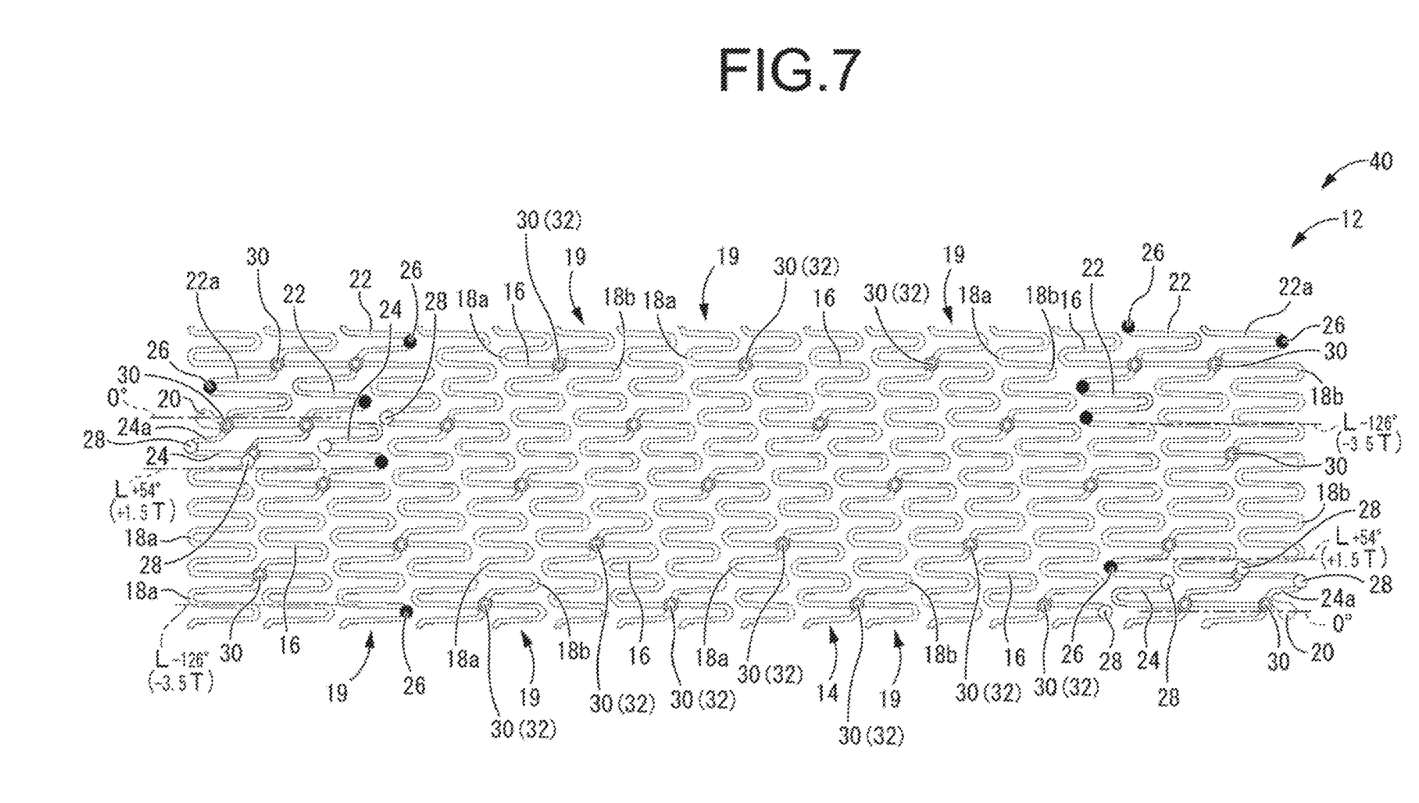
FIG. 7 is a developed view showing a stent as a second practical embodiment of the present invention by cutting to open the stent along one line on a circumference.

Next, FIG. 7 shows a stent 40 as a second practical embodiment of the present invention. In the preceding first practical embodiment, the number of waves (number of turns or number of periods) in the circumferential direction in one round of the stent (10), namely, the number of repeating units of the periodic structure in one round of the line-shaped body 14, is twelve (12 periods). However, in the stent 40 according to the present practical embodiment, the number of waves (number of turns or the number of periods) in the circumferential direction in one turn is ten (10 periods). Since the stent 40 of the present practical embodiment also adopts the structure similar to that of the preceding first practical embodiment, the similar effect can be achieved.

As shown in FIG. 7, in the stent 40 of the present practical embodiment, in the changing region of the inclination angle α of the helix of the line-shaped body 14 at the axially opposite side portions, there are provided narrow parts 28 comprising thinned curved parts and wide parts 26 comprising thickened curved parts within a range of +54 degrees to −126 degrees which corresponds to a range of +1.5 periods to −3.5 periods in the circumferential direction of the stent with respect to the reference position of 0 degrees, which is the distal end of the line-shaped body 14.

Figure 8:
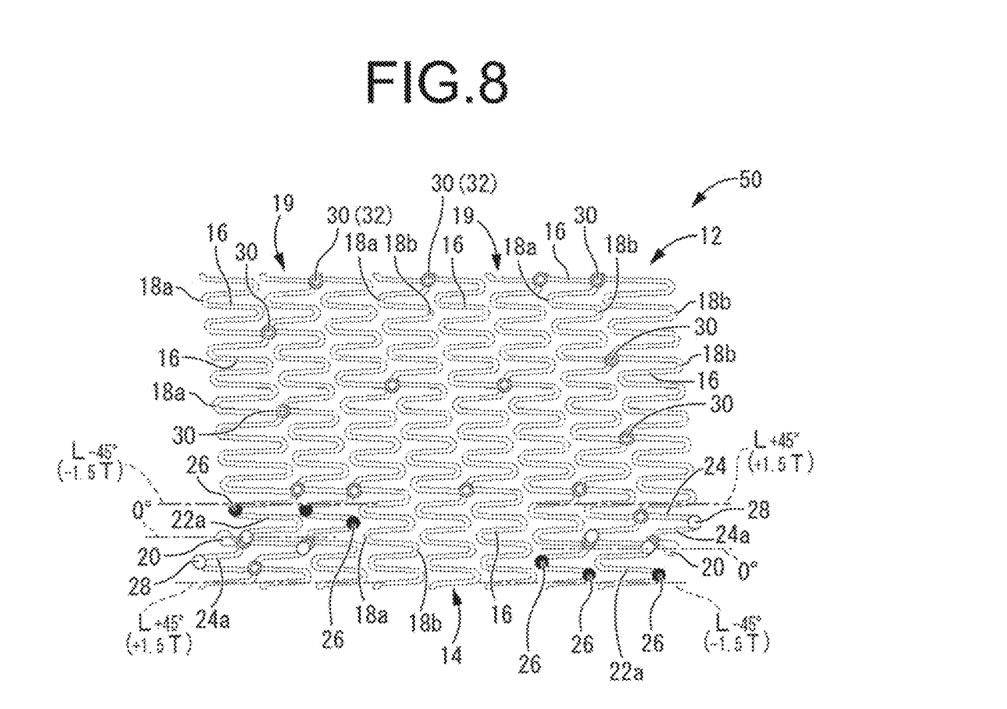
FIG. 8 is a developed view showing a stent as a third practical embodiment of the present invention by cutting to open the stent along one line on a circumference.

Furthermore, FIG. 8 shows a stent 50 as a third practical embodiment of the present invention. In the stent 50 of the present practical embodiment, the number of waves (number of turns) in the circumferential direction in one round is the same as in the preceding first practical embodiment, namely, twelve. On the other hand, in the preceding first and second practical embodiments, the entire axial dimension (entire length) of the stent (10, 40) is 18 mm, while in the stent 50 of the present practical embodiment, the entire axial dimension is 8 mm. Thus, the changing region of the inclination angle α of the helix of the line-shaped body 14 at the axially opposite side portions of the stent 50 is made shorter in the axial direction than that in the first and second practical embodiments. Besides, in the preceding first and second practical embodiments, the region where the wide part 26 is provided is a size of three rounds in the circumferential direction from the lengthwise end of the line-shaped body 14 at the axially opposite side portions of the stent, while in the present practical embodiment, the said region is a size of two rounds in the circumferential direction from the lengthwise end of the line-shaped body 14 (note that the narrow part 28 is provided over the region of one round in the circumferential direction from the lengthwise end of the line-shaped body 14). This configuration makes it possible to sufficiently obtain the region where the length dimension of the straight part 16 is roughly constant at the axially central portion of the stent 50.

As shown in FIG. 8, in the stent 50 of the present practical embodiment as well, in the changing region of the inclination angle α of the helix of the line-shaped body 14 at the axially opposite side portions, there are provided narrow parts 28 comprising thinned curved parts and wide parts 26 comprising thickened curved parts within a range of +1.5 periods to −3.5 periods in the circumferential direction of the stent with respect to the reference position of 0 degrees, which is the distal end of the line-shaped body 14. In the present practical embodiment in particular, the entire length of the stent and the changing region of the inclination angle α are made shorter in the axial direction than in the first practical embodiment. Thus, the narrow part 28 and the wide part 26 are provided in a range of +1.5 periods to −1.5 periods in the circumferential direction of the stent, and all the narrow parts 28 are arranged in a range of 0 degrees to +45 degrees, while all the wide parts 26 are arranged in a range of 0 degrees to −45 degrees. In the stent 50 of the present practical embodiment having such a structure as well, the structure similar to that of the preceding first practical embodiment is adopted, so that the similar effect can be achieved.

While the present invention has been described in detail hereinabove in terms of the practical embodiments, the invention is not limited by the specific disclosures thereof.

For example, in the preceding practical embodiments, in the stents 10, 40, 50, both the wide part (thick line part) 26 and the narrow part (thin line part) 28 are provided. However, it would be acceptable if only one of the thick line part (thickened curved part) and the thin line part (thinned curved part) is adopted. In the case where a plurality of the long parts 22 are provided, such a thick line part need not be provided to all the folded parts 18a/18b connected to the long parts 22, but is preferably provided to the folded part 18a/18b connected to at least one long part 22 among the plurality of the long parts 22. Similarly, in the case where a plurality of the short parts 24 are provided, it is preferable that the thin line part be provided to the folded part 18a/18b connected to at least one short part 24 among the plurality of the short parts 24. That is, the position where the thick line part and/or the thin line part is provided with respect to the entire stent can be appropriately set in consideration of the characteristics required of the stent, the place to be indwelled, or the like, and is not limited in advance.

Moreover, in the preceding practical embodiments, the wide part (thick line part) 26 whose width dimension is made larger than that of the long part 22 is provided over the entire length in the lengthwise direction of the folded part (curved part) 18a/18b connected to the long part 22. However, the wide part (thick line part) may be constituted by enlarging the width dimension of the folded part in part in the lengthwise direction. Similarly, the narrow part (thin line part) may be constituted by reducing the width dimension of the folded part (curved part) in part in the lengthwise direction. Alternatively, the portion whose width dimension is enlarged (thickened portion) may extend beyond the folded part (curved part) to reach the end of the straight part, or the portion whose width dimension is shortened (thinned portion) may extend beyond the folded part (curved part) to reach the end of the straight part.

Meanwhile, in the preceding practical embodiments, the wide part 26 serving as the thickened curved part and the narrow part 28 serving as the thinned curved part are formed by making the width dimension different from that of the folded parts 18a, 18b having the basic width dimension $W_1$ that are positioned in the axially central portion. However, it would also be acceptable that the thickened curved part and the thinned curved part are constituted by keeping the width dimension constant relative to the basic-thick folded parts that are positioned in the axially central portion while making the height dimension different therefrom. Alternatively, both the width dimension and the height dimension may be made different from those of the basic-thick folded parts that are positioned in the axially central portion.

That is, the thickness of the wide part 26 or the narrow part 28 is set relative to the basic-thick folded part 18a/18b provided to the axially central portion of the stent 10, and the specific thickness (cross-sectional area or cross-sectional shape) thereof is not limited, and for example, its relative relationship with the thickness of the straight part is not limited either.

Besides, in the preceding practical embodiments, the straight part 16 of the stents 10, 40, 50 has roughly constant width and height dimensions throughout the entire stents 10, 40, 50 so as to have a roughly constant cross-sectional area. However, the present invention is not limited to the said embodiment. Specifically, as long as the cross-sectional area of the straight part in the stent is roughly constant, the width dimension and the height dimension may be changed in the lengthwise direction.

Furthermore, in the present invention, the friable part that is preferentially broken during bending of the stent is not essential. That is, all the linking parts provided to the stent may have similar mechanical strength to that of the line-shaped body. Moreover, the linking part is not limited to what links the folded parts (curved parts) that are adjacent in the axial direction, but may link the folded parts that are remote in the circumferential direction, or may link the folded part and the straight part, or may link the straight parts to each other. Indeed, the linking part is not essential in the present invention.

Additionally, in the preceding practical embodiments, the folded parts 18a, 18b that connect the circumferentially adjacent straight parts 16, 16 have a curved shape that is a roughly semicircular arc shape. However, the folded parts 18a, 18b may have a bent shape that is a roughly overturned V-letter shape, or may be a roughly square-bracket shape, or the like. Also, the cross-sectional shape of the line-shaped body is not limited to a generally rectangular shape, but various cross-sectional shapes including a circular shape such as an oval, an ellipse, and a semicircle, and a polygonal shape and the like may be adopted.

Figure 9:
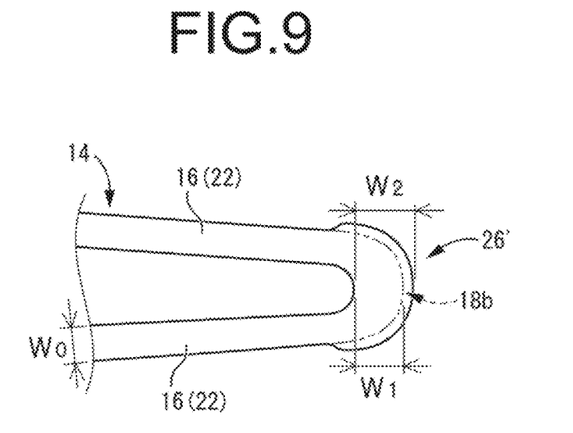
FIG. 9 is a view suitable for explaining another specific example of a wide part (thickened curved part) of a stent according to the present invention.
Figure 10:
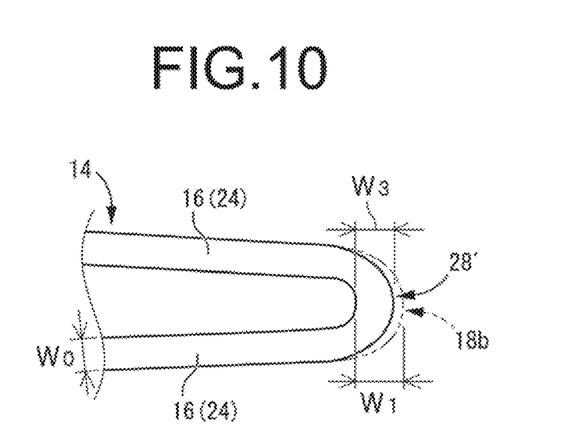
FIG. 10 is a view suitable for explaining another specific example of a narrow part (thinned curved part) of a stent according to the present invention.

Moreover, in the folded part (curved part), the specific shapes of the thickened portion (wide part) and the thinned portion (narrow part) are not limited to those in the preceding practical embodiments. That is, in the preceding practical embodiments, the wide part 26 and the narrow part 28 are formed by thickening or thinning the radially inner side of the curved shape of the folded part 18a/18b having the basic width dimension $W_1$. However, as shown in FIGS. 9 and 10, for example, the wide part 26' and the narrow part 28' may be formed by thickening or thinning the radially outer side of the curved shape of the folded part 18a/18b having the basic width dimension $W_1$.

Further, the axial dimension of the stent is not limited to 8 mm or 18 mm as exemplified in the preceding practical embodiments. Moreover, it would also be possible to appropriately increase or decrease the number of rounds of the portion where the inclination angle α of the helix is constant in the axially central portion of the stent (the portion where the length dimension of the straight part is roughly constant), and the portion where the inclination angle gradually changes, depending on the axial dimension of the stent, required characteristics, and the like.

In addition, the application range of the present invention is not limited to stents expanded by a balloon (balloon-expandable stents), but it is also applicable to those with a self-expansion function (self-expandable stents) by forming the stents with materials that exert a shape-memory effect such as Ni—Ti alloy, for example. More specifically, a stent that memorizes an expanded state, for example, can recover its original expanded state based on the shape-memory effect after insertion into the protection sheath in a contracted state to be constrained therein, while constraints against the stent by the protection sheath is released by removing the protection sheath from the stent at the indwelled position in the somatic lumen. Even in such a stent with a self-expansion function, the diameter can be enlarged roughly uniformly in the circumferential direction.

KEYS TO SYMBOLS 10, 40, 50: stent, 11: central axis, 14: line-shaped body, 16: straight part, 18a, 18b: folded part (curved part), 19: band-shaped body (winding portion), 22: long part, 24: short part, 26, 26': wide part (thick line part), 28, 28': narrow part (thin line part), 30: linking part

The invention claimed is:

1. A stent comprising a line-shaped body including a plurality of straight parts and a plurality of curved parts, the line-shaped body extending in a helical form in a circumferential direction while reciprocating in an axial direction by continuously alternating the plurality of straight parts and the plurality of curved parts, wherein:
   an entirety of the plurality of straight parts of the line-shaped body have a substantially constant thickness and width throughout the stent;
   the plurality of curved parts include:
      basic-thick curved parts that make up a largest number of the plurality of the curved parts in the stent and have a substantially constant width and thickness,
      a thickened curved part that is thicker than the basic-thick curved parts, and
      a thinned curved part that is thinner than the basic-thick curved parts;
   in a central portion of the stent along the axial direction, the plurality of straight parts have a roughly constant length dimension;
   in opposite end portions of the stent along the axial direction, the plurality of straight parts include a long straight part having a length that is longer than the roughly constant length dimension of the plurality of straight parts in the central portion of the stent, and the long straight part is connected to the thickened curved part; and
   in the opposite end portions of the stent, the plurality of straight parts include a short straight part having a length that is shorter than the roughly constant length dimension of the plurality of straight parts in the central portion of the stent, and the short straight part is connected to the thinned curved part.

2. The stent according to claim 1, wherein height dimensions of the plurality of straight parts and the plurality of curved parts of the line-shaped body are roughly constant.

3. The stent according to claim 1, wherein the long straight part is provided at a position approximately one round from a distal end of the line-shaped body in the circumferential direction of the stent.

4. The stent according to claim 1, wherein the thinned curved part is convex outward in the axial direction of the stent at a position closest to a lengthwise distal end of the line-shaped body.

5. The stent according to claim 1, wherein an inclination angle of a helix of the line-shaped body with respect to a central axis of the stent gradually increases toward an axial end thereof such that the inclination angle approaches a right angle with respect to the central axis of the stent.

6. The stent according to claim 1, wherein the line-shaped body further includes a linking part that links winding portions thereof to each other that are adjacent in the axial direction of the stent.

7. The stent according to claim 1, wherein at each axial end of the stent, when a lengthwise end of the line-shaped body is defined as a reference position of 0 degrees in the circumferential direction of the stent, with respect to a period of wave shape constituted by alternate continuation of the plurality of straight parts and the plurality of curved parts of the line-shaped body and reciprocating in the axial direction, the thinned curved part and the thickened curved part are provided within a range of +1.5 periods to −3.5 periods in the circumferential direction of the stent.

8. The stent according to claim 1, wherein each of the plurality of straight parts extends from a respective curved part of the plurality of curved parts in a length direction, and the length direction is orthogonal to the substantially constant thickness and width of the plurality of straight parts.

9. The stent according to claim 1, wherein the substantially constant thickness of the plurality of straight parts is a cross-sectional area that extends in a width direction and a height direction of the plurality of straight parts and is orthogonal to a length direction of the plurality of straight parts.

10. The stent according to claim 1, wherein the substantially constant width and thickness of the basic-thick curved parts is larger than the substantially constant width and thickness of the plurality of straight parts.

11. The stent according to claim 1, wherein lengthwise terminal ends of the line-shaped body formed on opposite axial ends of the stent are each provided with a disc part having a circular disk shape, and the short straight part is adjacent to the disc part in the circumferential direction.

12. The stent according to claim 1, wherein the thickened curved part and the thinned curved part are not directly joined to another curved part of the plurality of curved parts.

13. The stent according to claim 1, wherein:
   the line-shaped body includes:
      band-shaped bodies that each have a helical form in the circumferential direction, the band-shaped bodies being arranged adjacent to each other in the axial direction, and
      linking parts in which the band-shaped bodies that are adjacent to each other in the axial direction are joined together; and
   the thickened curved part and the thinned curved part do not form one of the linking parts.

14. The stent according to claim 1, wherein the long straight part, the thickened curved part, the short straight part, and the thinned curved part each form an axially outermost edge of an axial end of the stent in the axial direction.

* * * * *